United States Patent [19]

Leedle et al.

[11] Patent Number: 5,380,525
[45] Date of Patent: Jan. 10, 1995

[54] RUMINAL BACTERIUM FOR PREVENTING ACUTE LACTIC ACIDOSIS

[75] Inventors: Jane A. Z. Leedle, Manhattan, Kans.; Richard C. Greening; Walter J. Smolenski, both of Richland, Mich.

[73] Assignee: The Upjohn Company, Kalamazoo, Mich.

[21] Appl. No.: 920,599

[22] PCT Filed: Feb. 13, 1991

[86] PCT No.: PCT/US91/00857

§ 371 Date: Aug. 28, 1992

§ 102(e) Date: Aug. 28, 1992

[87] PCT Pub. No.: WO91/13146

PCT Pub. Date: Sep. 5, 1991

Related U.S. Application Data

[63] Continuation of Ser. No. 487,491, Mar. 1, 1990, abandoned.

[51] Int. Cl.$^6$ ................................. C12N 1/20
[52] U.S. Cl. ..................... 424/93.4; 435/140; 435/141; 426/2
[58] Field of Search ............. 424/93 D; 435/140, 141; 426/2

[56] References Cited

U.S. PATENT DOCUMENTS

| | | | |
|---|---|---|---|
| 3,857,971 | 12/1974 | Abdo | 426/53 |
| 3,956,482 | 5/1976 | Hahn | 424/93 |
| 4,138,498 | 2/1979 | Das | 426/2 |
| 4,172,127 | 10/1979 | Huber | 424/93 |

FOREIGN PATENT DOCUMENTS

| | | | |
|---|---|---|---|
| 2373237 | 7/1978 | France | A23K 1/18 |
| 2015334 | 10/1970 | Germany . | |
| 1251483 | 10/1971 | United Kingdom | C12K 3/00 |

OTHER PUBLICATIONS

K. Ogimoto et al., "*Genesis and Biochemistry of Rumen Acidosis 2. Microorganisms and Breakdown of Lactic Acid Isomers*", Chemical Abstracts, vol. 81, No. 17, p. 385, Abstract 103681z (1974).

M. J. Allison, et al., "*Ruminal Changes After Overfeeding with Wheat and the Effect of Intraruminal Inoculations on Adaptation to a Ration Containing Wheat*", J. Anim. Sci. 23:1164–1171 (1964).

P. T. Chandler, et al., "*Lactational Response of Dairy Cows Inoculated with Live Adapted Rumen Microorganisms*", J. Dairy Sci. 58(11):1660–1665 (1975).

*Primary Examiner*—Douglas W. Robinson
*Assistant Examiner*—Jean C. Witz
*Attorney, Agent, or Firm*—James D. Darnley, Jr.; Martha A. Gammill; Paul J. Koivuniemi

[57] ABSTRACT

This invention relates to a bacterial culture, NRRL B-18624, method for facilitating adaptation of ruminants from roughage or normal pasture diet to a higher energy diet, and a composition therefor comprising the bacterial culture.

4 Claims, No Drawings

RUMINAL BACTERIUM FOR PREVENTING ACUTE LACTIC ACIDOSIS

This application is a Rule 371 continuation of PCT/US91/00857, filed Feb. 13, 1991, which is a continuation of U.S. Ser. No. 07/487,491, filed Mar. 1, 1990, now abandoned.

FIELD OF INVENTION

This invention relates to novel microorganisms. More particularly, it relates to a lactic acid consuming ruminal bacterium which can prevent acute lactic acidosis, particularly in cattle abruptly switched from forage to concentrate (high grain) diets.

BACKGROUND OF THE INVENTION

Intensive beef production involves feeding energy dense, high concentrate diets to cattle. These concentrate diets contain a high percentage of corn, wheat, milo or other starchy components. When starter cattle are switched from forage to concentrate diets, acute indigestion can result, Elam, C. J., J. Anita. Sci., 43, pp. 898-901 (1976); Huber, T. L., J. Anita. Sci., 43, pp. 902-909 (1976); Uhart, B. A. and F. D. Carroll, J. Anim. Sci., 26, pp. 1195-1198 (1967). This indigestion is due to the rapid and extensive fermentation of the starch grain by the rumen microbial community which results in production of large amounts of organic acids, including lactic acid. The production of organic acids can be so great that the balances between ruminal acid production and utilization and ruminal buffering capacity are disrupted. This condition is termed acidosis. Acute acidosis is characterized by a rapid drop in pH and a sharp increase in the level of lactic acid in the rumen and in the blood, Elam, C. J., (supra); Slyter, L. L., J. Anim. Sci., 43, pp. 910-929 (1976); Uhart, B. A. and F. D. Carroll, (supra). If sufficiently severe, the over-production of lactic acid and other acids can contribute to a decrease in ruminal pH such that the normal microbial flora are upset. Often the result is that only a few bacterial species, which are tolerant of the acidic conditions, survive, Krogh, N., Acta Vet. Scand 2, pp. 102-119 (1961); Mackie, R. I. and F. M. C. Gilchrist, Appl. Environ. Microbiol., 38, pp. 422-430 (1979); Mann, S. O., J. Appl. Bacteriol., 33, pp. 403-409 (1970).

INFORMATION DISCLOSURE STATEMENT

To control the problem of acute lactic acidosis, several researchers have investigated adding viable lactate consuming bacteria or rumen bacteria from animals adapted to high grain diets, to the rumens of cattle that were abruptly changed from low to high concentrate diets, Allison, M. J., et al., J. Anim. Sci., 23, pp. 1164-1171 (1964); Chandler, P. T., et al., J. Dairy Sci., 38, pp. 1660-1665 (1975); Cook, M. K., et al., Am. J. Vet. Res., 38, pp. 1015-1017 (1977); Huber, T. L., Am. J. Vet. Res., 35, pp. 639-641 (1974). They predicted that the added bacteria would consume the higher levels of lactate produced, maintaining the balance between production and consumption and thereby lessening or eliminating the problem of acidosis. Allison et al. and Huber, supra, found that if the rumen of a roughage fed animal was inoculated with rumen fluid from a high concentrate adapted animal the problem of acute acidosis was alleviated when the abrupt shift of ration was made. U.S. Pat. No. 4,138,498, refers to feeding rumen bacterial cultures from an animal adapted to a concentrate diet to a roughage adapted animal then fed a concentrate diet, and claims a reduction or elimination of the symptoms of lactic acidosis. Increases in weight gains and feed conversions also were alleged in cattle receiving these cultures as compared to control cattle. U.S. Pat No. 3,857,791, refers to rumen inoculation with "adapted rumen microorganisms," or a mixture of *Megasphaera elsdenii* and *Selenomonas ruminantium* to reduce or eliminate the symptoms of lactic acidosis during the adaptation of ruminants to high grain rations. Additionally, it has been reported that milk production was increased by the intraruminal inoculation of certain live adapted rumen microorganisms to dairy cows, Chandler et al., supra; U.S. Pat. No. 3,956,482.

Despite the fact that these documents describe these methods of preventing acidosis or aiding the adaptation of cattle to high concentrate diets, no related product has been marketed to date. To overcome the problems referred to above, we have isolated a specific lactic acid consuming rumen bacterium from concentrate fed cattle for use as ruminal inocula to prevent acidosis in cattle abruptly switched from a high forage to a high concentrate ration.

SUMMARY OF THE INVENTION

The present invention relates to a bacterial culture, NRRL B-18624. The bacterium is characterized in that it consumes lactic acid, is resistant to monensin, lasalocid 2-deoxy-glucose (2-DG) and low pH (5.3), it uses lactate in the presence of other sugars and it produces butyrate. Culture NRRL B-18624 is also referred to herein as isolate 407A and as culture UC-12497.

The invention also relates to a composition for facilitating the adaptation of ruminants from roughage or normal pasture rations to a high energy starch ration, consisting essentially of the bacterial culture NRRL B-18624.

Also disclosed is a method of facilitating the adaptation of ruminants from a roughage or normal pasture ration to a high energy ration comprising administering to said ruminant an amount of a bacterial culture, NRRL B-18624, during said adaptation.

Also disclosed is a method of preventing acute lactic acidosis in ruminant animals comprising administering to said ruminant an amount of a bacterial culture NRRL B18624 sufficient to prevent such acidosis.

DETAILED DESCRIPTION OF THE INVENTION

EXAMPLE 1

Isolation and Enrichment of Ruminal Lactic Acid Consuming Bacteria

Animals and diets: Hereford X Angus crossbred steers were used. Four animals were fed a ration of 60% cracked corn, 30% silage and 10% B282 supplement (Table 1) at maintenance level once daily. Three rumen-fistulated crossbred cattle were fed a ration of 90% B-376 and 10% chopped hay (Table 2) at maintenance once daily. Animals had free access to water at all times.

Media: Anaerobic dilution solution (ADS) was prepared according to the methods of Bryant, M. P. and L. A. Burkey, J. Dairy Sci., 36, pp. 205-212 (1953). Inoculations and transfers of bacteria were performed in an anaerobic glove box (Coy Lab. Products, Ann Arbor, Mich. atmosphere: 85% $N_2$, 10% $H_2$ and 5% $CO_2$, ambient temperature). All media were prepared under 100% $CO_2$ by methods described previously, Bryant, M. P., Am. J. Clin. Nutr., 25, pp. 1324-1328 (1972);

Hungate, R. E., Academic Press, New York (1966). Media for the study are listed in Table 3. Differential carbohydrate medium plates were prepared as the L medium but without lactate and with 0.2 to 0.5% of the following compounds: glucose, maltose, mannitol or soluble starch (Difco). 2-deoxy-D-glucose (2-DG, grade II, Sigma) was added to the L medium at 0.5%, and monensin or lasalocid was added to L medium with a final concentration of 6 ppm. A series of media (designated B) was prepared without rumen fluid and with varying pH values and reducing solutions (media B 1, B2, B3 and B 14). For other tests, ultra-clarified rumen fluid was added back to the B media and designated B11-R, B12-R, and B13-R (Table 3).

Collection of rumen fluid: For in vitro enrichments, rumen fluid was collected 2 to 5 hours after feeding from the four animals on B282 supplement. For direct plating experiments, rumen fluid was collected 5 hours after feeding from the three animals on B-376 supplement. All rumen contents samples were collected under a flow of $CO_2$ into flasks and held on ice until delivered to the laboratory. Each animal was represented a separate source for potential bacterial isolations.

Enrichments and plating: In the in vitro enrichments, equal weights of rumen fluid and 2% (w/w) amylopectin (Sigma A-7780) in ADS were mixed under $CO_2$ and 10 ml aliquots of each of the 4 prepared rumen fluid:1% amylopectin mixtures was pipeted into 50 ml serum bottles and sealed with slotted rubber stoppers. Bunsen valves were inserted through the stoppers to relieve excess pressure. After 4 hours of incubation at 38° C., 0.55 ml of the bottle contents was added to 5 ml B2 medium and incubated for 18 hours. Ten-fold dilutions were made of each of the four enrichments which were transferred to fresh B2 daily for 3 consecutive days. Afterwards, serial tenfold dilutions from each source were made in B3 medium to $10^{-9}$. The $10^{-5}$ to $10^{-9}$ dilutions were plated (0.1 ml/plate) onto B2 agar medium. Plates were incubated at 38° C. for 5 days under 5 p.s.i. $CO_2$.

For the direct plating experiments, ten-fold dilutions (to $10^{-9}$) of the rumen fluid collected from each of the 3 animals on B-376 supplement were made in B14 medium. One tenth ml aliquots of each dilution series ($10^{-5}$ to $10^{-9}$) were plated onto B14 agar and incubated as above.

Isolation sequence: Well isolated, representative colonies were picked and spotted onto L agar plates in an array that corresponded to grids on a stainless steel replicator. Plates were incubated for 48 hours as above. Growth on the L agar plates served as the "master" plates and was used to inoculate the differential plates with the replicator.

Characterization of isolates: The scheme for selection of the lactic acid consuming isolates is presented in Chart 1. Initially, the isolates were tested for carbohydrate utilization and resistance to 6 ppm monensin or lasalocid. Those isolates that did not grow on L medium in the presence of either of the two antibiotics were eliminated. Those that grew in the presence of monensin or lasalocid were grown on lactate at pH 5.3 in B2 broth to test for low pH tolerance. Those isolates that did not grow were eliminated. Those that grew in B2 medium at pH 5.3 were assessed for their fermentation acid profiles in B2 broth. Growth rates of the isolates were determined in L broth. Finally, media with low level lactate (0.55 mm B11-R, B12-R and B13-R) in the presence and absence of 0.2% glucose or maltose were inoculated to determine if lactate was utilized in the presence of these two sugars.

Analytical: Volatile fatty acids (VFA) analysis was by standard methods. Lactic acid concentrations were determined by the method of Barker, S. B. and W. H. Summerson, J. Biol. Chem., 138, pp. 535–554 (1941).

The enrichment and direct plating techniques yielded lactic acid consuming rumen bacterial isolates. From the enrichment step, the B2 medium selected for those isolates that could grow rapidly on lactate at pH 5.3. The pH of the liquid in the in vitro enrichment bottles after 4 hours of incubation, (at which time aliquots from the bottle cultures were transferred into B2) was 5.1 to 5.4.

For the direct plating experiments, isolates were grown on the low pH medium (B14) in the presence of monensin and 2-DG. This medium selected for those lactate utilizers that were resistant to 6 ppm monensin and could grow in the presence of 2-DG at pH 5.3. 2-DG was chosen as a selective agent because it can inhibit those organisms that transport glucose or maltose as well as lactic acid (Romano, A. H. et al., J. Bacteriol., 139, pp. 93–97 (1979); Thompson, J. Biochimie, 70, pp. 325–336 (1988)).

A total of 142 colonies from both the enrichment and direct plating isolation techniques was picked and evaluated on the differential carbohydrate plates. From these, 14 representative isolates from the enrichment series and 8 from the direct plating series were tested as outlined in Chart 1. Ten of the 22 isolates were retained for further testing. Substrate utilization profiles of these 10 are shown in Table 4. Isolates #252 through 320 grew poorly on soluble starch. Mannitol was included because relatively few rumen bacteria can metabolize it. Mannitol differentiates two important rumen lactate utilizing species, *Megasphaera elsdenii* and *Selenomonas ruminantium*, from lactate utilizing bacteria that do not use it.

Of the 6 isolates tested, all except #298 grew well on mannitol. All 10 grew well on lactate medium in the presence of compounds that inhibit other bacteria (monensin, lasalocid, and 2-DG). Monensin and lasalocid were included as selection criteria because these ionophore antibiotics are currently fed to feedlot cattle. Most rumen lactate utilizing bacteria are resistant to at least 48 ppm of these antibiotics (Dennis, S. M. et at., J. Animi. Sci., 52, pp. 418–426 (1981)).

Growth curves of typical isolates in L medium were measured. Specific growth rates and generation times, respectively, ranged from 0.187 and 3.71 h for isolate #394 to 0.644 and 1.08 h for isolate #382 (Table 5).

When the isolates were grown on the B2 lactate medium the major VFA produced were butyric and propionic acids with minor amounts of valeric and isovaleric acids (Table 6). The negative values for acetate and isobutyrate indicate their utilization. Large amounts of butyrate were produced by all of the isolates except #394. Small amounts of caproic acid were produced by most of the isolates.

Lactate consumption in low lactate media (0.55 mM initial concentration) in the presence and absence of maltose or glucose was measured. Lactate was utilized by the isolates even in the presence of either of the two sugars. The apparent differences in initial concentration of DL-lactic acid in the cultures containing carbohydrate were due to an interference of the sugars with the lactate assay. In all 5 isolates tested, the initial concentration of lactic acid (35 μg/ml) was reduced 60% to approximately 15 μg/ml after 24 hours. The isolates also fermented the added glucose or maltose since the background absorbance value decreased with time.

Morphologically, all the isolates were either large cocci, (1.2 μm) occurring as singles or pairs, or coccobacilli (1.0×3.0 μm). This information along with resistance to lasalocid and monensin at 6 ppm, suggests that the isolates resemble *M. elsdenii* (Holdeman, L. V. et at., Anaerobe Laboratory Manual, 4th ed., Virginia Polytechnic Institute and State University, Blacksburg, (1977); Krieg, N. R. and I. G. Holt, Bergey's manual of systematic bacteriology, Vol. 1, Williams and Wilkins, Baltimore, (1984)).

In summary, using enrichment and direct plating techniques, we isolated 10 lactic acid consuming rumen bacteria. These isolates are resistant to monensin, lasalocid, 2-deoxy-glucose and low pH (5.3). Most grow as well on glucose, maltose and mannitol as they do on lactate, but they continue to utilize lactate even in the presence of these sugars. All the isolates produce butyrate, an unexpected result since morphologically they resemble *M. elsdenii* which produces propionate.

TABLE 1

| Animal Diet | |
|---|---|
| Ingredients | % in diet[1] |
| Cracked corn | 60 |
| Corn silage (Harvestore) | 30 |
| B-282 protein supplement[2] | 10 |

[1]On a dry matter basis
[2]Contains the following:

TABLE 1-continued

| | % by wt. |
|---|---|
| Soybean oil meal, 49% | 57.145 |
| Alfalfa meal, dehydrated, 17% | 17.000 |
| Molasses, dried | 17.000 |
| Yellow tallow, stabilized | 2.000 |
| Defluorinated phosphate (CDP), 18% P | 1.500 |
| Limestone, ground | 1.900 |
| Salt | 2.000 |
| Trace Mineral Mix (CCC, 10% Zn) | .250 |
| Vitamin A, 30,000 IU/gram | .100 |
| Vitamin D, 15,000 IU/gram | .005 |
| Vitamin E, 20,000 IU/lb | .050 |
| Sodium selenite, .2 mg/g | .050 |

TABLE 2

| Animal Diet | |
|---|---|
| Ingredients | % as fed |
| B-376[1] | 90 |
| Hay, chopped to 3" lengths | 10 |

[1]Contains the following:

| | % by Wt. |
|---|---|
| Corn rolled (8.5 as is) | 89.639 |
| Soybean meal (48.5% as is) | 6.758 |
| Fat (animal) | 0.973 |
| Dical (18.5%) | 0.200 |
| Limestone | 1.298 |
| Salt | 0.291 |
| Dyna K (Potassium Chloride) | 0.600 |
| Selenium premix (0.2%) | 0.048 |
| Trace mineral premix | 0.096 |
| Vitamin A (30,000 IU/gram) | 0.007 |
| Vitamin D (15,000 IU/gram) | 0.002 |
| Vitamin E (20,000 IU/lb) | 0.088 |

TABLE 3

| Media Composition | Medium[1] | | | | | | | | |
|---|---|---|---|---|---|---|---|---|---|
| | L | B | B1 | B2 | B14 | B3 | B11-R | B12-R | B13-R |
| | g or ml per l | | | | | | | | |
| Mineral I, ml | 37.5 | 37.5 | 37.5 | 37.5 | 37.5 | 37.5 | — | — | — |
| Mineral II, ml | 37.5 | 37.5 | 37.5 | 37.5 | 37.5 | 37.5 | — | — | — |
| Resazurin, 0.1% solution, ml | 1.0 | 1.0 | 1.0 | 1.0 | 1.0 | 1.0 | — | — | — |
| Trypticase (BBL), g | 2.0 | 2.0 | 2.0 | 2.0 | 2.0 | 2.0 | — | — | — |
| Yeast Extract (Difco), g | 1.0 | 0.5 | 0.5 | 0.5 | 0.5 | 0.5 | — | — | — |
| VFA Solution, ml | 10.0 | 10.0 | 10.0 | 10.0 | 10.0 | 10.0 | — | — | — |
| Hemin Solution, ml | 10.0 | 10.0 | 10.0 | 10.0 | 10.0 | 10.0 | — | — | — |
| Trace minerals, ml | 10.0 | 10.0 | 10.0 | 10.0 | 10.0 | 10.0 | — | — | — |
| Vitamin Solution, ml | — | 10.0 | 10.0 | 10.0 | 10.0 | 10.0 | — | — | — |
| DL-Lactate Solution A[2], ml | 50 | — | 50 | 50 | 50 | — | — | — | — |
| Acetic Acid, ml | — | — | — | 1.2 | 1.2 | 1.2 | — | — | — |
| Sodium acetate, anhydrous, g | — | — | — | 6.5 | 6.5 | 6.5 | — | — | — |
| Reducing agent[3], ml | 10 | 10 | 10 | — | — | — | — | — | — |
| Sodium carbonate, 8% solution, ml | 50 | 50 | 50 | — | — | — | — | — | — |
| DL-Lactate solution B[4], ml | — | — | — | — | — | — | 10 | 10 | 10 |
| Ultra clarified rumen fluid[5], ml | 100 | — | — | — | — | — | 1000 | 1000 | 1000 |
| Distilled water, ml | 780 | 830 | 780 | 840 | 830 | 890 | — | — | — |
| Cysteine HCl.H$_2$O, g | — | — | — | 0.5 | 0.5 | 0.5 | 0.25 | 0.25 | 0.25 |
| Glucose, g | — | — | — | — | — | — | — | 2.0 | — |
| Maltose, g | — | — | — | — | — | — | — | — | 2.0 |
| 2-deoxy-D-glucose, g | — | — | — | — | 5 | — | — | — | — |
| Monensin solution[6], ml | — | — | — | — | 10.0 | — | — | — | — |
| Final pH | 6.8 | 6.8 | 6.8 | 5.3 | 5.3 | 5.3 | 5.8 | 5.8 | 5.8 |

[1]All media were prepared under 100% CO$_2$. Agar was added at 1.75–2.0% w/v for solid media.
[2]DL-Sodium lactate 60% syrup (Baker):83.3 g, qs to 500 ml with distilled water to give a 10% w/v solution. Final concentration in the media was 0.5% w/v.
[3]Reducing agent: 2.5% each of cysteine HCL.H$_2$O and Na$_2$S.9H$_2$O - added after boiling the medium and before autoclaving.
[4]DL-Sodium lactate 60% syrup (Baker): 1.0 ml mixed in 332.3 ml distilled water to give 1.8 mg/ml. Final concentration in media B11-R, B12-R and B13-R was 200 μM (0.0018%).
[5]Rumen fluid was collected from concentrate fed steers, 5 hours after feeding, autoclaved, centrifuged and passed through a 0.2 μM filter.
[6]Monensin solution: Final concentration in medium was 6 ppm.

TABLE 4

Growth of lactate utilizing isolates on various substrates[1]

| Isolate | None[2] | Lactate | Glucose | Maltose | Mannitol | Sol. Starch | Monensin | Lasalocid | 2-DG[3] |
|---|---|---|---|---|---|---|---|---|---|
| 252 | + | ++ | — | +++ | +++ | + | ++ | ++ | ++ |
| 280 | + | ++ | — | +++ | ++++ | + | ++ | ++ | ++ |
| 298 | + | ++ | — | ++ | + | + | ++ | ++ | ++ |
| 310 | + | ++ | — | +++ | +++ | + | ++ | ++ | ++ |
| 314 | + | ++ | — | +++ | +++ | + | ++ | ++ | ++ |
| 320 | + | ++ | — | +++ | +++ | + | ++ | ++ | ++ |
| 382 | + | ++ | +++ | +++ | — | — | +++ | +++ | +++ |
| 394 | + | ++ | ++ | + | — | — | ++ | ++ | +++ |
| 407 | + | ++ | ++ | +++ | — | — | ++ | ++ | ++ |
| 414 | + | ++ | +++ | + | — | — | ++ | ++ | +++ |

[1]Degree of growth on agar plates:
— = Not determined, + = very slight growth, ++ = good growth, +++ = heavy growth, ++++ = luxuriant growth
[2]L medium without lactate
[3]Monensin and lasalocid at 6 ppm; 2-DG at 0.5%, adjusted to pH 5.8

TABLE 5

Growth rate determinations of several lactate utilizing bacteria[1]

| Isolate | Specific Growth Rate | Generation Time (h) |
|---|---|---|
| 382 | 0.644 | 1.08 |
| 394 | 0.187 | 3.71 |
| 407 | 0.580 | 1.19 |
| 414 | 0.543 | 1.27 |

[1]Isolates grown in L medium

TABLE 6

Volatile fatty acid profiles of lactate utilizing bacteria grown in B2 medium[1]

| Isolate | Acetic | Propionic | Iso-butyric | Butyric | Iso-valeric | Valeric |
|---|---|---|---|---|---|---|
| 252 | −47.86 | 5.56 | −0.30 | 21.51 | 0.73 | 2.82 |
| 280 | −46.08 | 8.83 | −0.36 | 17.61 | 0.32 | 2.37 |
| 298 | −48.21 | 6.34 | −0.46 | 19.23 | 0.47 | 2.57 |
| 310 | −43.94 | 5.70 | −0.52 | 22.83 | 0.47 | 2.78 |
| 314 | −46.17 | 5.28 | −0.52 | 21.90 | 0.43 | 2.67 |
| 320 | −62.38 | 0.44 | −0.28 | 28.75 | 0.85 | 3.17 |
| 382 | −40.63 | 3.54 | −0.38 | 32.08 | 0.84 | 3.09 |
| 394 | −13.18 | −4.51 | −0.58 | 4.29 | −0.28 | 1.75 |
| 407 | −50.38 | −4.34 | −0.38 | 43.92 | 0.80 | 2.93 |
| 414 | −40.21 | 2.47 | −0.30 | 34.61 | 0.94 | 3.16 |

[1]Net production of acids, compared with uninoculated B2 medium.

---

Chart 1. Scheme for Selection of Lactate Utilizing Bacteria

Representative colonies from enrichment or direct plating
↓
Test for carbohydrate use and growth on lactate in presence of 6 ppm monensin or lasalocid
↓
Re-streak for purity on L medium
↓
Test for low pH tolerance
↓
Assess fermentation acids after growth on lactate
↓
Utilization of 50 μg/ml (0.55 mM) lactate in presence of 0.2% glucose or maltose (B11-R, B12-R and B13-R)
↓
Store isolates in B medium with 20% w/v glycerol, at −153° C.

EXAMPLE 2

In vitro Acidosis Test System to Assess Lactic Acid Consumption by Lactate Consuming Ruminal Bacteria This example shows the development of an in vitro test system to mimic the acidotic process in rumens and to use it to select strains of lactic acid consuming rumen bacteria for use as ruminal inocula to prevent acidosis in vivo.

The in vitro test system is summarized as follows: Ruminal fluid, collected from forage fed animals, is mixed (50:50) with 2% (wt/vol) amylopectin in anaerobic dilution solution and incubated with shaking at 38° C. for 12 h. The response variables, pH and lactic acid concentrations, are measured at hourly intervals. During the incubation period, the pH of the rumen fluid mixture decreases to <6.0 and lactic acid accumulates to >35 mM within 6 h. These responses are similar to those observed in the rumens of cattle switched from forage- to grain-based diets. We used this in vitro system to test selected strains of lactic acid consuming rumen bacteria (Example 1) for their ability to prevent the decrease in pH and (or) the increase in lactic acid. Criteria for success were maintenance of pH above 6.0 and at least an 80% reduction in the amount of lactic acid produced relative to uninoculated controls. Six anaerobic, lactic acid consuming bacteria previously isolated from the rumens of grain fed cattle from Example 1 were tested. Four strains met the criteria for success. These 4 strains were further compared with respect to growth rate on lactic acid, lactic acid consumption in the presence of sugars, and sensitivity to antibiotics commonly used in the feedyard. Through this test scheme, 2 strains were selected: #320 and #407.

Animals and diets: Hereford X Angus crossbred steers fed high forage diets (>70% alfalfa hay or corn silage, dry matter basis) fed ad libitum, were used. Ruminal contents were collected by stomach tube (non-fistulated animals) or by rumen fistula. Animals had free access to water at all times. For each experiment, ruminal fluid was collected from 3 animals.

Media: Amylopectin (Sigma) was prepared as a 2% (wt/vol) suspension in anaerobic dilution solution (ADS, 5). Strains of lactic acid consuming bacteria were maintained on B1 medium containing 0.5% (wt/vol) sodium (DL−)lactate. Inoculations and transfers of bacteria were performed in an anaerobic glove box (Coy Lab. Products, Ann Arbor, Mich.; atmosphere: 85% $N_2$, 10% $H_2$ and 5% $CO_2$, ambient temperature). All media were prepared under 100% $CO_2$ by methods described previously (Example 1).

In vitro acidosis test procedure: Ruminal contents samples were collected 1.5 h postfeeding under a flow of $CO_2$ into flasks and held on ice until delivered to the laboratory. Ruminal samples were strained through 2 mm nylon mesh, pooled in equal weights, and chilled on ice for 20 min. When added, 400 ml of B1 broth cultures of the test strains of lactic acid consuming bacteria were grown to mid-log phase, harvested by anaerobic centrifugation, and resuspended in 14 ml ADS for use as inoculants. Under a flow of $CO_2$, 10 ml pooled rumen fluid and 0.5 ml bacterial inoculant (or 0.5 ml ADS) were placed in 60 ml serum bottles, sealed with gray stoppers, and chilled on ice. Twenty two bottles were filled for each strain (control or treatment) tested. When the last bottle was filled, all bottles were fitted with bunsen valves and placed in a rotary shaker-incubator (New Brunswick, 160 rpm) at 38° C. The bottles were allowed to equilibrate 20 min, then 2 bottles of each treatment were collected at 0, 2, and at hourly intervals thereafter through 12 h.

Growth measurements: Growth rates of selected strains were compared on B15 broth medium. B15 was a modification of the basal (B) medium previously described (Example 1), and contained additionally (percentage in final medium): sodium lactate (99.5+% L-lactate, Baker, 0.18%), glucose (0.2%), and maltose (0.2%). Optical densities were measured at 650 nm in a Perkin-Elmer spectrophotometer, Model 55, with a path length of 18 min.

Analytical: The pH was recorded after transferring the bottle contents to a plastic centrifuge tube and immersing a standard combination pH electrode. Then the samples were frozen at −20° C. for later analysis of fermentation acids. Lactic acid concentrations were determined by the methods of Barker, S. B. and W. H. Summerson, supra; or a modification thereof. Both the D(−) and L(+) forms of lactic acid were measured unless otherwise stated. References to lactic acid in this report are to the total of D(−) and L(+) forms. Volatile fatty acids were analyzed as described previously in Example 1.

Antibiotic susceptibility: Minimal inhibitory concentrations (MICs) of selected antibiotics were determined following NCCLS guidelines (National Committee for Clinical Laboratory Standards, Approved standard M11-A: reference agar dilution procedure for antimicrobial susceptibility testing of anaerobic bacteria, National Committee for Clincial Laboratory Standards, Villanova, Pa. (1985)) with Wilkins-Chalgren agar medium (Difco) containing 1% (vol/vol) reducing agent (2.5% L-cysteine hydrochloride/2.5% sodium sulfide, wt/vol). The following antibiotics were tested: NAXCEL Sterile Powder (The Upjohn Co.), oxytetracycline (P-L Biochemicals), erythromycin (Sigma), penicillin G (Sigma), lincomycin (hydrochloride, The Upjohn Co.), tylosin (tartrate, Sigma), rifampin (Sigma), thiopeptin (Fugisawa), thiostrepton (Sigma), and chlortetracycline (ICN Nutritional Biochemicals). NAXCEL Sterile Powder, penicillin G, lincomycin, and tylosin were dissolved in water. All others were dissolved in DMSO. Antibiotic concentrations were prepared from 0.25 to 128 μg/ml (or Units/ml) correcting for the specified purity of each agent, or, if no information was available, the purity was assumed to be 100%. Three strains of anaerobic bacteria were included in the MIC determination as positive controls (known MICs for the antibiotics used). These bacteria were: *Bacteroides fragilis* ATCC 25285, *Bacteroides thetaiotaomicron* ATCC 29741, and *Clostridium perfringens* ATCC 13124.

The decrease in pH to below 6.0 and increase in lactic acid concentration to above 35 mM was reproducible among replicate bottles and between experiments. Preliminary evaluations of candidate strains of ruminal lactic acid consuming bacteria were conducted on the "best" 6 strains of lactic acid consuming bacteria identified through our selection scheme in Example 1.

Rumen fluid for Experiment #8 was collected from all pasture fed animals. Test strain numbers #310, #320, and #382 were compared against ADS-inoculated control bottles. The pH of the control bottles of the incubating rumen fluid-amylopectin mixture declined after 3 h from its initial value of 6.7 to 5.8 at 6 h. Thereafter the pH remained below 6.0. Meanwhile, the concentration of lactic acid in the control bottles increased from the level of detection (ca. 0.5 mM) to 39 mM at 6 h. The concentration of lactic acid decreased after 6 h to 24 mM at 12 h. In bottles inoculated with any of the three test strains, the pH of the incubating mixture remained above 6.0, and the concentration of lactic acid never rose above 7 mM (4–5 h). Any lactic acid produced was consumed by the isolates within a 3 h period.

Fermentation acids produced during the incubation period also were measured. Fermentation acid accumulation plateaued after 6 h but comparisons were made at 12 h. Total acid concentrations at 12 h were 468 mM in the control bottles, and 542, 511, and 526 mM for strains #310, #320, and #382, respectively. In the uninoculated control bottles, acetate, propionate, butyrate and valerate were present at 59, 24, 15, and 2 molar percent, respectively. With the test strains added, these molar percentages changed to (averages of) 50, 17, 26, and 7%, respectively. All test strains yielded similar fermentation acid profiles. On average, bottles with added test strains produced 58 mM more total acids compared to control bottles. Lactic acid in the control bottles comprised a portion of this difference (at 12 h) although it is likely that the fermentation in the control bottles was limited in extent by the low pH after 6 h.

Rumen fluid for the next Experiment was collected from all pasture fed animals. Test strains #394, #407 and #414 were compared against ADS-inoculated control bottles. The pH of the control bottles declined after 4 h from its initial value of 6.8 to 5.7 at 6 h. As in the previous Experiment, the pH remained below 6.0 thereafter. In this experiment, test strains #407 and #414 kept the pH above 6.0, whereas strain #394 did not. Lactic acid began to accumulate in the bottles after 4 h of incubation. The concentration of lactic acid in the control bottles increased from the level of detection to 45 mM at 6 h. After 6 h, the control bottle concentration of lactic acid remained around 45 mM until 12 h when the concentration increased to 66 mM. With strains #407 and #414 added, lactic acid accumulated to 15 mM by 6 h but within an hour was consumed to the level of detection. With strain #394 however, lactic acid accumulated to 36 mM at 6 h and only gradually decreased to 12 mM at 12 h.

In this second Experiment the fermentation acids were more variable; individual acid concentrations did not plateau after 6 h as they had in the first Experiment. Total acid concentrations at 12 h were 476 mM in the control bottles, and 513, 561, and 579 mM for strains #394, #407, and #414, respectively. In the control bottles, acetate, propionate, butyrate and valerate were present at 63, 26, 9, and 1 molar percent, respectively. With test strain #394 added, these molar percentages were 62, 17, 11, and 10%, respectively. With strains #407 and #414 added, these molar percentages were 45, 15, 30 and 10%, respectively. On average, bottles with added test strains produced 75 mM more total acids compared to control bottles. If strain #394 is omitted, strains #407 and #414 each produced an average of 94 mM more total acids than did control bottle fermentations. As before, the concentration of lactic acid in the control bottles comprised a potion of this difference although it is likely that the control bottle fermentations were limited by low pH.

None of the 6 strains tested in this in vitro incubation system produced propionate, the preferred fermentation product (based on positive correlation with improved animal performance), as the predominant fermentation acid. All appeared to produce large amounts of butyrate which decreased the molar percentages of acetate and propionate by 30%. Likewise, the presence of added test strains increased the molar percentages of butyrate and valerate by 2- to 3-fold and 3- to 10-fold, respectively. These data agree with the fermentation acids produced by these test strains in pure culture (Example 1).

Five of the 6 test strains maintained the pH of the bottle contents above 6.0 which is advantageous for the continuance of a balanced ruminal fermentation. Continuance of the fermentation under these conditions was supported by the higher total acid concentrations in the bottles containing test strains compared to control bottles (including lactic acid).

More importantly however, lactic acid produced by the indigenous rumen bacteria on the added amylopectin (starch substrate) was consumed by 5 of the 6 added test strains of lactic acid consuming bacteria. We chose the best strains from the two Experiments for further evaluation. These were strains #320, #382, #407, and #414.

These 4 were assessed for their ability to consume lactic acid in the presence of glucose and matlose (medium B15). Comparisons of their growth curves and consumption rate of lactate and glucose showed that all strains grew as fast or at a faster rate than other rumen bacteria. Generation (doubling) times in B15 medium were 0.93, 1.21, 0.87, and 1.56 h for strain #320, #382, #407, and #414, respectively. All 4 strains were able to cometabolize lactate and glucose (maltose concentrations in the medium were too low to allow interpretation), although #320 and #407 used both substrates at faster rates. Thus, strains #320 and #407 with doubling times of 1 h or less were "better" than #382 and #414. Their faster growth rates might enable them to better compete in the rumen.

The minimal inhibitory concentrations for the 4 selected strains were determined with an array of antibiotics (Table 7). The MIC results can be interpreted as the same within plus or minus two 2-fold dilutions. Data for the control microorganisms agreed with their known MICs. We found strain differences for NAXCEL Sterile Powder, erythromycin, penicillin G, lincomycin and tylosin. All 4 test strains were equally sensitive to rifampin and were tolerant of oxytetracycline, thiopeptin, and thiostrepton (Table 7). Strain #414 was the most tolerant to tylosin, a common cattle feed additive, while strain #320 was most sensitive to lincomycin, a common swine feed additive.

We selected strains #320 and #407 for further evaluation as potential acute acidosis preventatives based on the results of the in vitro lactic acidosis tests, strain growth rates, and the MIC data.

Methods for administering microbial cultures to animals are well known to those in the art (see e.g., U.S. Pat. No. 4,138,498 which is incorporated herein by reference.)

TABLE 7

| | Minimal inhibitory concentrations (μg/ml) of selected antibotics[1] | | | | | | |
|---|---|---|---|---|---|---|---|
| | Reference Strains | | | | | | |
| | ATCC 25285 | ATCC 29741 | ATCC 13124 | Lactic acid utilizing test strains | | | |
| Antibiotic | B. Fragilis | B. theta. | Cl. perf. | #407 | #320 | #382 | #414 |
| Naxcel ® | 128 | >128 | 16 | 16 | >128 | 8 | 32 |
| Oxytetracycline | 1 | 64 | ≦0.25 | 32 | 128 | 64 | 64 |
| Erythromycin | 64 | 64 | 8 | 32 | 8 | 32 | 128 |
| Penicillin G | 64 | 64 | 1 | 8 | 128 | 2 | 64 |
| Lincomycin | 32 | 64 | 1 | 32 | ≦0.25 | 32 | 32 |
| Tylosin | 8 | 16 | 2 | 16 | 16 | 16 | 128 |
| Rifampin | 0.5 | 2 | ≦0.25 | 4 | 2 | 4 | 4 |
| Thiopeptin | 128 | >128 | ≦0.25 | >128 | >128 | >128 | >128 |
| Thiostrepton | 128 | >128 | ≦0.25 | >128 | >128 | >128 | >128 |
| Chlortetracycline | 1 | 16 | ≦0.25 | 16 | 64 | 32 | 32 |

[1]Method as in (17). Penicillin in units/ml.

EXAMPLE 3

Characterization and Presumptive Identification of Ruminal Lactate Utilizing Bacterium 407A.

Ruminal lactate utilizing bacterial isolate 407A (NRRL B-18624; UC-12497) and two strains of *Megasphaera elsdenii* (strains B 159 and ATCC 25940) were characterized according to published guidelines. Isolate 407A was similar to *M. elsdenii* strain B 159 and the type strain ATCC 25940 in that it was a large, non-motile, gram-negative coccus that produced isobutyric, butyric, isovaleric, valerie and caproic acids. Hydrogen was produced by all three bacteria from the metabolism of lactate. All grew at pH 5.4 on lactate but only isolate 407A grew on lactate at pH 5.0 in the presence of 6 ppm monensin. All converted threonine to propionate, were indole negative, did not reduce nitrate or hydrolyze starch. Isolate 407A was inhibited by bile whereas 25940 and B159 were not. Strain B159 produced acid in, media containing glucose, maltose or mannitol but 407A did not, whereas type strain 25940 produced only weak acid from maltose and mannitol. The results obtained for isolate 407A show that it is similar to the descriptions of *M. elsdenii*. However, growth of 407A in lactate-containing media at pH 5.0 in the presence of monensin may place this bacterium in a taxonomic group other than *M. elsdenii*.

Bacteria and their cultivation: Strain 407A (UC-12497) was isolated according to Examples 1 and 2 and was stored under liquid nitrogen. The type strain of *Megasphaera elsdenii*, strain number 25940, was received from the American Type Culture Collection, Rockville, Md. and was originally isolated from the rumen of a sheep. Strain B159 was obtained from the culture collection of Dr. M. P. Bryant, Univ. of Illinois and also was originally isolated from a sheep rumen. All strains were routinely cultivated on B18 medium (Table 8) at 38° C. under a $CO_2$ headspace.

Test media: Commercial preparations of anaerobic peptone yeast extract fermentation media conforming to the formulations and methods of the Virginia Polytechnic Institute (V.P.I.) Anaerobe Laboratory manual, Holdeman, L. V., E. P. Cato and W. E. C. Moore (ed.). Anaerobe laboratory manual, 4th ed., Virginia Polytechnic Institute and State University, Blacksburg, were purchased from Carr-Scarborough Microbiologicals, Inc. (Stone Mountain, Ga). Low pH lactate containing media were prepared without and with 0.5% 2-deoxy-D-glucose or 6 ppm monensin and designated B20, B21 and B22 respectively (Table 8). The final pH values of the B20, B21 and B22 media were 5.43, 5.65 and 5.04, respectively.

Procedures: Young (7 h) cultures grown in B18c were used to determine the Gram stain and to inoculate chopped meat carbohydrate (CMC) medium (Carr-Scarborough Microbiologicals, Inc.). The CMC cultures were incubated overnight (17 h) and then used to inoculate the test media tubes (4 drops/tube) and B18c agar plates. The tubes were inoculated under $CO_2$ to comply with the V.P.I. methodology, Holdeman, L. V., et al., supra. The stoppers were removed under a flow of anaerobic grade $CO_2$, the tubes were inoculated and then resealed. After the tubes were incubated statically and upright at 38° C. for 46 to 47 h they were opened, the pH of the contents was measured and the appropriate biochemical tests were performed (Table 9).

Analytical: Measurement of pH was done with a Corning Model 12 pH meter equipped with a Corning semi-micro combination electrode, model 476541. PY lactate cultures were assayed for D(−) and L(+) lactic acid. PY basal, lactate, glucose and threonine cultures were analyzed for volatile fatty acids via flame ionization gas chromatography. Hydrogen was measured with a gas chromatograph equipped with a thermal conductivity detector using conditions similar to those described by Nelson, D. R. and J. G. Zeikus, Appl. Environ. Micro., 28, pp. 258–261 (1974).

The biochemical tests chosen for the identification of 407A were based on the key for anaerobic genera of bacteria as described in the V.P.I. manual, Holdeman, L. V., et al., supra. The key in the manual indicates that strain 407A is likely from the Megasphaera genus because it is a large gram-negative coccus producing isobutyric, butyric, isovalerie, valerie and caproic acids. Consequently, those tests were done which would sufficiently differentiate Megasphaera from all the other characterized anaerobic cocci. Additionally, we knew that isolate 407A would grow in the low pH, lactate-containing media (B20, B21 and B22). We tested these media to see if they were inhibitory to *M. elsdenii* strains 25940 and B159.

Results of the biochemical tests and VFA analyses used to characterize the bacteria are presented in Table 9. Examination of the three strains via phase contrast microscopy revealed large (ca. 2.3 μm diameter) cells that occurred singly, in pairs or short chains. In older cultures, chains were more commonly seen. All three bacteria stained gram-negatively. Surface colonial morphologies after 2 days of incubation for the three strains were similar. They were 2 to 3 mm in diameter, circular and entire, buff colored, and had a butter-like consistency.

All bacteria failed to produce acid when cellobiose, esculin, lactose, starch, sucrose and xylose were the carbon sources in the test media. Catalase was not detected, esculin was not hydrolyzed and all were obligately anaerobic. None of the bacteria digested meat, reduced nitrate, hydrolyzed starch, produced indole or were motile. B159 produced more acid in glucose, maltose and mannitol than did 407A and 25940. Bile inhibited growth of 407A, but not of the other two strains. All grew well on lactate at pH 5.3–5.7 in the presence or absence of 2-deoxy-D-glucose, but only 407A grew at pH 5.0 in the presence of 6 ppm monensin. Threonine was converted to propionate by all three bacteria. Hydrogen was produced by all three at levels of 6.2, 12.9 and 26.7% for 407A, 25940 and B159, respectively. VFA profiles were similar for each microorganism grown on the basal, lactate, glucose and threonine media. Butyrate was the main fermentation end product in the three bacteria tested. This is in agreement with data reported by others for *M. elsdenii*.

The tests unique to strain 407A were 1) its lack of acid production from glucose, maltose and mannitol, 2) its poorer growth in the presence of bile and 3) growth in lactate containing medium at pH 5.0 in the presence of 6 ppm monensin (Table 9). Acid production (or the lack of it) from carbohydrates by a bacterium is one of the key traits for its identification. Only the tests done for B159 fully conformed to the results in the V.P.I. manual. The type strain 25940 did not fully conform because glucose was negative, and maltose and mannitol produced only intermediate amounts of acidity ("weak acidity", Table 9).

Only two other genera of the anaerobic cocci, Veillonella and Acidaminococcus are gram negative. Isolate 407A differs from Veillonella because it is much larger, produces isobutyric, burytic, isovaleric and caproie acids and converts threonine to propionate. It differs from Acidaminococcus because the latter is smaller, does not produce caproute and does not utilize lactate. Thus, the characteristics of isolate 407A are more comparable with the taxonomy of *M. elsdenii*, but because it can grow well at pH 5.0 in the presence of monensin, 407A may be a new species or subspecies of the genus Megasphaera.

The phylogenetic relationship of Megasphaera to other anaerobic cocci is poorly known, Hill, G. B., (1981) The anaerobic cocci, pp. 1631–1650, In M. P. Starr, H. Stolp, H. G. Truper, A. Balows and H. G. Schlegel (ed.), The prokaryotes: a handbook on habitats, isolation, and identification of bacteria. Springer-Verlag, New York; Rogosa, M., Anaerobic gram-negative cocci, pp. 680–685. In N. R. Kreig and J. G. Holt (ed.), Bergey's manual of systematic bacteriology, vol. 1. The Williams & Wilkins Co., Baltimore, (1984). To date, only one species of Megasphaera is known, *M. elsdenii*. Although there are some discrepancies between the results of our tests and those of the V.P.I. manual, there may not be enough evidence at this point to support that 407A is other than a new strain of *M. elsdenii*. However, identification of isolate 407A on the basis of biochemical tests done in this study should be regarded as presumptive.

TABLE 8

Composition of B18c, B20, B21, and B22 media

| | Amount per liter | | | |
|---|---|---|---|---|
| | B18c | B20 | B21 | B22 |
| sodium lactate, 60% syrup[a] | 16.7 g | 16.7 g | 16.7 g | 16.7 g |
| Mineral 1[b] | 37.5 g | 37.5 ml | 37.5 ml | 37.5 ml |
| Mineral 2[c] | 37.5 g | 37.5 ml | 37.5 ml | 37.5 ml |
| resazurin (0.1% solution) | 1.0 ml | 1.0 ml | 1.0 ml | 1.0 ml |
| Trypticase (BBL) | 5.0 g | 5.0 g | 5.0 g | 5.0 g |
| Peptone (Bacto, Difco) | 5.0 g | 5.0 g | 5.0 g | 5.0 g |
| Yeast extract (Difco) | 5.0 g | 5.0 g | 5.0 g | 5.0 g |
| Distilled water boil under $CO_2$, cool, then add: | 865.0 ml | 910.0 ml | 910.0 ml | 910.0 ml |
| cysteine HCL.$H_2O$ | 0.5 g | 0.5 g | 0.5 g | 0.5 g |
| sodium carbonate (8% wt./vol, prepared under $CO_2$) | 50.0 ml | — | — | — |
| Acetic acid | — | 1.2 ml | 1.2 ml | 1.2 ml |
| Sodium acetate (anhydrous) autoclave at 121° C. for 20 min | — | (1.3 g) 6.5 g[d] | (1.3 g) 6.5 g[d] | (1.3 g) 6.5 g[d] |
| 2-deoxy-D-glucose | — | — | 5.0 g[e] | — |
| Monensin solution[f] | — | — | — | 10 ml |

[a]Sodium lactate: Sigma No. L-1375 - contained approximately equal amounts of D(−) and L(+) isomers
[b]Mineral 1:6 g $K_2HPO_4$ per liter distilled water
[c]Mineral 2:6 g $KH_2PO_4$; 6 g $(NH_4)_2SO_4$; 12 g NaCl; 2.45 g $MgSO_4.7H_2O$ and 1.59 g $CaCl_2.2H_2O$ per liter distilled water
[d]pH of medium adjusted to 5.2 before autoclaving
[e]Prepared in an anaerobic glovebox with deoxygenated water, and then added aseptically to sterile, but cooled medium by using filtration.
[f]Added 32.4 mg monensin sodium (Sigma M-2513) to 50 ml 200 proof ethanol. Mixed then added filter sterilized solution to sterile medium. Final concentrations of monensin was 6 ppm.

TABLE 9

Tests and methods used for the characterization of bacterial isolate 407A and *Megasphaera elsdenii*, strains 25940 and B159.[a]

| Test | Media[b] | Procedures and interpretation |
|---|---|---|
| pH | Basal (PY) +: cellobiose esculin glucose lactose maltose mannitol starch sucrose xylose | measure 48 h culture with pH electrode - if pH >6.0 then score as negative (−), if pH 5.5 to 6.0 then score as weak acid (w), if pH <5.5 then score as strong acid (a). |
| bile | glucose + bile | compare growth to PY glucose - record as inhibited (no growth), growth (+ to ++++) or stimulated (growth better than in PY glucose). |
| catalase | chopped meat | add 0.5 ml culture to small tube - add 0.5 ml 3% $H_2O_2$ - continuous bubbles = +. |
| esculin hydrolysis | esculin | add 3 drops 1% ferric ammonium citrate - black color = +. |
| growth aerobically | B18c agar | streak plates with overnight culture, incubate aerobically, check for growth, 48 h. |
| growth on lactate at pH 5.4 | B20 | record as inhibited (no growth) or growth (+ to ++++). |
| growth on lactate at pH 5.6 in presence of 2-DG | B21 | record as inhibited (no growth) or growth (+ to ++++). |
| growth on lactate at pH 5.0 in presence of 6 ppm monensin | B22 | record as inhibited (no growth) or growth (+ to ++++). |
| hydrogen production from lactate | B18c | measure % $H_2$ in the headspace. |
| indole | indole nitrate | 2 ml culture +1 ml xylene, mix, let stand 2 min. Slowly add 0.5 ml Erlich's reagent. Pink color = positive, yellow = negative. |
| lactate utilization | lactate | measure total lactate - compare with uninoculated PY lactate and in PY basal - decrease in lactate = utilization (+). |
| meat digestion | chopped meat | disintegration of meat particles = positive reaction. Incubate 14–21 days. |
| motility | B18c | observe 4–6 h culture via phase contrast microscopy. |
| nitrate reduction | indole nitrate | add 1 ml nitrate Reagent A and 0.5 ml nitrate Reagent B to culture. Red = positive (nitrite present). If no red color, add Zn dust - red color = negative, no color = complete reduction. |
| starch hydrolysis | starch | add 2 or 3 drops of Gram's iodine to culture. Observe immediately. Black = no hydrolysis. |
| VFA profiles from: | PY basal glucose lactate threonine | gas chromatography - compare results with uninoculated media - if acids produced in amounts > 1 meg./100 ml then the abbreviation for that acid capitalized, if acids produced in amounts < 1 meg./100 ml then the abbreviation for that acid is presented in lower case. Abbreviations as in the V.P.I. manual (5). |

[a]Most tests and procedures as described in the V.P.I. anaerobe laboratory manual (5).
[b]Pre-reduced, anaerobically sterilized media - see Appendix for formulation.

TABLE 10

Biochemical reactions and gas chromatographic profiles for lactate utilizing isolate 407A and *Megasphaera elsdenii* strains 25940 and B159[a]

| | Reactions/Profiles | | |
|---|---|---|---|
| Test | isolate 407A | strain 25940 | strain B159 |
| gram stain | — | — | — |
| colonial morphology | 2–3 mm dia. circular, entire, biege, butyrous | 2–3 dia. circular, entire, biege, butyrous | 2–3 mm dia. circular, entire, biege, butyrous |
| pH in: | | | |

TABLE 10-continued

Biochemical reactions and gas chromatographic profiles for lactate utilizing isolate 407A and *Megasphaera elsdenii* strains 25940 and B159[a]

| Test | isolate 407A | strain 25940 | strain B159 |
|---|---|---|---|
| PY (basal) | − | − | − |
| cellobiose | − | − | − |
| esculin | − | − | − |
| glucose | − | − | a |
| lactose | − | − | − |
| maltose | − | w | a |
| mannitol | − | w | a |
| starch | − | − | − |
| sucrose | − | − | − |
| xylose | − | − | − |
| bile | + | ++++ | ++++ |
| catalase | − | − | − |
| esculin hydrolysis | − | − | − |
| growth aerobically | − | − | − |
| growth at pH 5.4 | ++++ | ++++ | ++++ |
| growth at pH 5.6 in presence of 2-DG | ++++ | ++++ | ++++ |
| growth at pH 5.0 in presene of 6 ppm monesin | ++++ | ± | ± |
| hydrogen production from lactate[b] | 6.2 | 12.9 | 26.7 |
| indole | − | − | − |
| lactate utilization | + | + | + |
| meat digestion | − | − | − |
| motility | − | − | − |
| nitrate reduction | − | − | − |
| starch hydrolysis | − | − | − |
| threonine conversion to propionate | + | + | + |
| VFA from:[c] | | | |
| PY (basal) | p, ib, b, iv, v, c | p, ib, b, iv, v, c | a, p, ib, b, iv, v, c |
| lactate | A, P, ib, B, iv, V, c | A, P, ib, B, iv, V, c | A, P, ib, B, iv, v, c |
| threonine | p, ib, b, iv, v, c | p, ib, b, iv, v, c | a, p, ib, b, iv, v |
| glucose | a, p, ib, b, iv, v, c | a, p, b, ib, iv, v, c | a, p, ib, B, iv, v, c |

[a]Refer to Table 2 and text for interpretation and keys. Methods based on those of the V.P.I manual (5).
[b]Percent $H_2$ in the head space.
[c]Compared to uninoculated media.

EXAMPLE 4

This example summarizes data from 3 pairs of animals ruminally inoculated with strain 407A, each pair inoculated at a different time during acidosis induction, compared to their contemporary (block) controls.

Experimental design: The parent study was designed based on an in vivo model of acute lactic acidosis. Four blocks of 4 animals each were used. Each block was separated in time by 2 to 4 weeks. In each of blocks 2, 3 and 4, two additional ruminally fistulated steers were added to make a group of 6. Steers were randomly assigned to either control or inoculated (407A-dosed) treatment groups. Block 1 was not included as 407A cells were unavailable. The data summarized below were derived from the steers in blocks 2, 3 and 4.

Animals and their management: Hereford x Angus crossbred steers were used. These cattle (about 300 to 380 kg body weight) were ruminally fistulated, housed in motels and fed ad libitum a low quality alfalfa hay-wheat straw diet (5:2; minimal gain of 0.1 to 0.2 kg per day) for a minimum of three weeks. Just prior to use, each animal was weighed (Table 11). Subsequent feedings of chopped hay or acidsis-inducing grain meals were based on this bodyweight (BW).

Feeding regimen and rumen sampling: Cattle were moved into the measurement room in the afternoon prior to the experimental period and not fed until the following day. Water was available thwughout the feeding and fasting period. On Day 1, the animals were fed 0.5 % BW meals consisting of chopped alfalfa at 7 AM and 3 PM and at 7 AM on Day 2. Any feed remaining was delivered intraruminally via the fistula. No feed was offered on Day 3. Acute acidosis was initiated on Day 4 starting at 6 AM. The fistula was opened and two 5 ml samples of ruminal contents were collected, frozen immediately in plastic tubes immersed in dry ice-ethanol, and stored at −20° C. for lactate and volatile fatty acid (VFA) analysis. Ruminal pH was measured with an immersible flat surface electrode (Sensorex 450C, Stranton, CA) and an MP-815 pH meter (Fisher Scientific) with the probe held approximately midpoint in the rumen. Immediately following, the first of four 0.5% BW meals consisting of 90% ground corn and 10% molasses, hand-mixed with an equal weight of water, was introduced as a bolus dose into each rumen via the fistula. The remaining meals were delivered similarly at 7, 8 and 9 AM. In addition to the rumen samples collected at 6 AM, subsequent rumen samples were obtained through the fistula at intervals after bolus dosing. In such cases, no more than 1250 ml of ruminal fluid was collected per animal after the pH had been measured.

Animal recovery after initiation of acidosis: After the last sample from each animal was taken, the steers were offered chopped hay ad libitum. The following day, the animals were returned to the motels where they had free access to long hay and minimal supplement.

Preparation of Strain 407A for ruminal inoculation: Lactic acid consuming ruminal bacterium strain 407A (UC-12497) was grown in static culture on medium B18c (Table 8) at 37° C. Routine transfers were done using (crimp seal) serum tubes (5 ml medium/tube). Using a 1% inoculum level, an overnight culture was used to inoculate 2, 60 ml broths in 100 ml serum bottles. These scale up cultures were incubated 6 to 7 h and then used to inoculate a 20 l glass carboy containing 12 l of B 18c medium. The inoculated carboy was incubated statically overnight (16 to 18 h) at 37° C. After that time a sample was withdrawn aseptically for OD measurement (650 nm, path length 18 mm) and for viable count determination (see below).

Anaerobic harvesting and preservation of viable cells: 407A cells were harvested by anaerobic centrifugation. Air-fight, o-ring sealed, centrifuge bottles (Du-Pont), deoxygenated by previous equilibration within an anaerobic glovebox, were used. The bottles were filled in the glovebox using house vacuum to dispense the carboy culture, balanced (weighed) and sealed. The bottles then were centrifuged at $6,250 \times$ g in a CS-3 rotor (Sorvall) for 20 rain at room temperature. In the glovebox, the supernatants were discarded and the pelleted cells were resuspended in a small amount of B18c medium with no lactate but with 20% (v/v) glycerol. After all the pellets were resuspended, the suspensions were pooled, the total volume recorded, and a viable count determination made as described below. The avenge total volume of concentrated cell suspension from each 12 l carboy was 123 ml representing about a 100-fold concentration factor. The B18c-glycerol cell suspensions were distributed into 100 ml serum bottles and frozen at $-70°$ C. Maximum time frozen before use was 3 weeks. Viability tests showed that the frozen suspensions were stable for at least 3 months. Immediately after thawing and prior to inoculation of the suspension into cattle, another viable count was made.

Viable count determination: One ml of culture or concentrated cell suspension was serially diluted in 10-fold steps in ADS buffer (Bryant, M. P. and L. A. Burkey, J. Dairy Sci., 36, pp. 205–217 (1953)). B18c agar (1.5% w/v) plates were inoculated with 50 and 100 $\mu$l quantifies of selected dilutions. The plates were incubated at 38° C. under 5 lbs. $CO_2$ for 48 h in stainless steel incubation vessels and then the colonies were counted to the population of viable cells in the culture or fresh or thawed cell suspensions.

Selection of ruminal dose: Previously, we determined that an inoculation level of $2 \times 10^8$ viable cells per ml was an effective dose to reduce the accumulation of lactic acid and to prevent a decrease in pH in vitro. Thus, we targeted this concentration for our in vivo dose level. Since actual rumen volumes of the experimental steers were unknown, we assumed that each had a nominal liquid volume of 30 l. The target was to inoculate $6 \times 10^{12}$ viable 407A cells per rumen, or approximately $2 \times 10^8$ viable cells per ml ruminal fluid. Since each carboy yielded a different volume and viability of 407A cells, concentrated cell suspensions from 3 carboys were combined for each block. Thus, in addition to being inoculated at a different time after acidosis induction, each block received a slightly different dose (see Table 12).

Rumen inoculation procedure: On the day of acidosis initiation for each experimental block, concentrated cell suspensions from 3 separate carboy cultures were thawed at room temperature and combined in the anaerobic glovebox. A viable count of the combined suspension was determined Crable 12). The suspension subsequently was divided into 2 equal portions (one for each of the 2 experimental animals) and sealed in erlenmeyer flasks. These were removed from the glovebox and, at the designated time, opened within the ruen and thoroughly hand-mixed with the ruminal contents of each animal. The inoculum was ready for ruminal administration no earlier than 30 min ahead of time. The treated animals received their ruminal inoculum at 4, 3 and 2 h after the initiation (0600 h) of acidosis in blocks 2, 3 and 4, respectively.

Analytical procedures: Lactic acid concentrations were determined using the method previously described. Volatile fatty acid concentrations were determined via an HPLC method (Dionex Corporation, Ion chromatography cookbook: a practical guide to quantitative analysis by ion chromatography, pp. Il15–16 (1987)).

In block 2 the treated cattle were inoculated at 4 h post-initiation of acidosis. Strain 407A had previously been shown to reduce the in vitro accumulation of lactic acid at this timepoint.

In block 2, ruminal pH decreased rapidly in the control animals, from a mean of about 8.0 to below 5.0 within 6 h after the initiation of acute acidosis. Ruminal pH in the 2 steers dosed with strain 407A also declined to 5.0 by 6 h but then stayed at pH 5.0 or above for the remaining time while the control animals' pH continued to decrease.

Ruminal lactic acid in the control animals accumulated to over 100 mM between 4 and 8 h post-acidosis induction, and lactic acid remained high throughout the remaining observation period. Ruminal lactate accumulated in the dosed steers rose to about 60 mM between 4 and 6 h post-acidosis induction. Thereafter, lactic acid concentrations continually decreased to less than 20 raM.

Ruminal concentrations of VFAs were monitored for the first 12 h. Before acidosis induction, very little mminal fermentation activity was present in any of the experimental animals. For example, acetate concentrations were about 10 mM. Ruminal fermentation activity, reflected in acetate accumulation, increased steadily with each meal. Between 5 and 12 h, the ruminal acetate concentration in the control animals steadily declined to a level of about 5 mM. This temporal decrease coincided with the large increase in lactic acid production. In contrast, ruminal acetate concentrations in 407A-dosed steers increased over the first 6 h then appeared to hold at 28 mM over the 12 h interval monitored.

Very low levels of propionate, butyrate and valerate (less than 5, 2 and 1 mM, respectively) were detected in control animals over the observation period. However, after ruminal inoculation at 4 h with strain 407A, propionate increased about 8-fold. An 8-fold increase also was observed for butyrate and valerate both of which increased steadily from the 4 h timepoint, reaching mean concentrations of 14 and 4.5 mM, respectively, by 12 h. Less than 1 mM concentrations of isobutyrate and isovalerate were observed in control or dosed animals.

In block 3, mininat inoculation time was moved up one hour; the animals were inoculated 3 h post-initiation of acidosis.

Ruminal pH in the control animals again decreased rapidly from a mean of 8.4 to less than 5.0 within 9 h post-acidosis induction. Ruminal pH in the dosed steers however, decreased less rapidly than in block 2 and remained around 5.5. A low mean pH value of 5.2 was reached at the 16 h timepoint for the dosed steers. Ruminal lactic acid concentrations in control steers again climbed above 100 mM between 4 and 8 h and remained high. In dosed animals, lactate concentrations rose to about 45 mM between 4 and 6 h but declined after 12 h to near zero by 24 h.

In control steers, ruminal acetate concentrations rose during the period of meal feeding but fell off thereafter as in block 2, while acetate concentrations remained around 20 mM in the dosed steers. Propionate, butyrate and valerate concentrations in control animals again were quite low (less than 5, 2 and 1 mM, respectively). In the dosed steers, propionate increased 5-fold after 5 h post-acidosis initiation while butyrate and valerate increased steadily about 10-fold each after 3 h, the time of ruminal inoculation. Less than 1 mM concentrations of isobutyrate and isovalerate were observed in control or dosed animals.

With the analysis of the lactic acid samples being completed from the earlier blocks, it appeared that 407A was able to metabolize lactate immediately upon inoculation and did not appear to suffer if the ruminal concentration of lactic acid was low. With the success of inoculating one hour earlier in block 3, the ruminal inoculation time was moved up one additional hour for block 4 to 2 h post-acidosis induction.

In block 4, mechanical failure caused the loss of ruminal pH data. Ruminal lactic acid concentrations showed that induction of acute acidosis was as successful as in previous blocks. Control animals again showed the rapid accumulation of ruminal lactic acid between 4 and 8 h post-acidosis induction. However, inoculation with 407A 2 h post-acidosis induction, appeared to arrest most of the lactic acid accumulation. The highest level detected in dosed steers was less than 20 mM at 5 to 6 h. The lactic acid concentration was less than 4 mM thereafter.

In block 4, the profiles of acetate concentration in both control and dosed steers were similar to those of previous blocks although the dosed steers' acetate concentration was higher. Propionate, butyrate and valerate concentrations in control animals were similar to those of previous blocks. In contrast to previous blocks, little propionate was produced in the dosed animals. However, butyrate and valerate increased steadily about 40-fold from the 2 h time of ruminal inoculation in dosed steers to 50 and 10 mM, respectively. Less than 1 mM concentrations of isobutyrate and isovalerate were observed in control or dosed animals.

The acidosis animal model used in this example was used to test the lactic acid consuming bacterium 407A. First, the animals were backgrounded on a very low quality diet, then fed hay at 1% BW, and then starved for 24 h prior to acidosis induction. This predisposed these steers to very low levels of endogenous ruminal fermentation activity typified by high ruminal pH (>8.0) possibly due to excess bicarbonate, lower amounts of $CO_2$ produced and low concentrations of VFAs. Second, the introduction of grain meals (2% BW total) into this system initiated metabolism of the surviving ruminal microbes evidenced by the steady increase in all major VFAs over the first 4 h. After 4 h however, it was obvious that the faster growing, lactic acid producing microbes had overwhelmed their VFA-preducing counterparts, and a lactic acid fermentation was established. Third, although there was some variability in the time required for the ruminal pH to drop below 5.0 and the lactic acid concentration to increase above 100 mM, the model was consistent. Introduction of lactic acid consuming bacterium 407A into this (lactic) acidosis model was a rigorous test of its integrity and metabolism.

In block 2, 407A was inoculated at 4 h post-acidosis induction. This timepoint coincided with the greatest rates of decrease in ruminal pH and increase in ruminal lactic acid. Except for the fact that the ruminal pH did not decline below 5.0, we concluded that 407A was inoculated too late to have a significant effect on pH. In block 3, with ruminal inoculation at 3 h after initiation of acidosis induction, the effect on ruminal pH was more obvious. Block 3 data indicated a mean ruminal pH of 5.5 or above in 407A-dosed animals. Due to technical difficulties, block 4 pH data could not be included. However, the differences in pH between control and 407A-dosed steers may have been even greater because the lactic acid levels in these dosed animals were much less than those in block 3.

The effect of 407A on lactic acid accumulation was large in all blocks tested. In block 2, not only did its concentration reach half that of control animals, but lactic acid was continually reduced with time in the 407A-dosed animals. These data indicated that frozen and thawed 407A cells were capable of immediate lactic acid metabolism upon ruminal inoculation. With the earlier inoculations of blocks 3 and 4, ruminal lactic acid accumulations were effectively blocked by 407A, thus acute lactic acidosis conditions did not develop.

As mentioned, low VFA concentrations were present in all animals prior to acidosis induction. In acidotic control animals, the increase in major VFAs was replaced by lactic acid after 4 h post-induction. Regardless of the time of ruminal inoculation of 407A-dosed animals, butyrate and valerate, the major fermentation products of 407A when grown on lactate, increased immediately after inoculation. The increase in propionate followed 1 to 2 h later in blocks 2 and 3.

Butyrate levels were highest when propionate levels were lowest (block 4). In contrast, butyrate levels were lowest when propionate levels were highest (block 2). When the rumens were dosed at the 4 h timepoint (block 2), the soluble sugar concentration (mostly glucose and maltose) was high, nearly 50 mM. Thus, sugars as well as lactic acid were available to 407A. In block 4 when the rumens were inoculated at the 2 h timepoint, correspondingly less sugar and more lactic acid was available for fermentation. Since 407A also can grow on some sugars these ruminal conditions may be responsible for the differences in VFA profiles observed. This phenomenon has been observed previously in vitro with Megasphaera elsdenii, Marounek, M., et al., Appl. Environ. Microbiol, 55, pp. 1570–1573 (1989). M. elsdenii can utilize several substrates simultaneously and make propionate, butyrate and valerate, Marounek, M., et al., supra, and Russell, J. B. and R. L. Baldwin, Appl. Environ. Microbiol., 36, pp. 319–329 (1978).

In summary, prevention of acute lactic acidosis was progressively more successful in terms of maintaining a more neutral ruminal pH and low lactic acid concentration, when the rumen was inoculated with $1-2 \times 10^8$ viable 407A cells per ml ruminal fluid, 4, 3 and 2 h after acidosis induction. From these data it appears that lactic acid consuming bacterium 407A UC-12497) is useful as an acidosis preventative or adaptation aid.

Isolate 407A has been deposited at The Upjohn Culture Collection, The Upjohn Company, Kalamazoo, Mich. 49001 and has been assigned deposit number UC-12497. Isolate 407A was also deposited at the ARS Patent Culture Collection, Agricultural Research Service Culture Collection, Northern Regional Research Center, 1815 North University Street, Peoria, Ill. 61604 on Feb. 15, 1990 under accession number NRRL B-18624.

TABLE 11

| | | | | Animal numbers, body weights, meal size and the time of ruminal inoculation | | |
|---|---|---|---|---|---|---|
| Block no. | Experiment date | Trial animal no. | Actual animal no. | Body weight (kg) | 0.5% BW meals (kg) | Time of ruminal inoculation[a] |
| 1 | 30 | 1 | 2046 | 355 | 1.6[b] | ND[c] |
|   | March | 2 | 2063 | 325 | 1.4 | |
|   | 1989 | 3 | 2102 | 338 | 1.4 | |
|   |   | 4 | 2011 | 354 | 1.6 | |
| 2 | 18 | 5 | 2099 | 317 | 1.6 | |
|   | April | 6 | 2049 | 357 | 1.8 | |
|   | 1989 | 7 | 2051 | 336 | 1.7 | |
|   |   | 8 | 2030 | 329 | 1.6 | |
|   |   | 101 | 2093 | 364 | 1.8 | 4 |
|   |   | 102 | 2028 | 337 | 1.7 | 4 |
|   |   | 9 | 2088 | 370 | 1.8 | |
| 3 | 03 | 10 | 2040 | 388 | 1.9 | |
|   | May | 11 | 1087 | 364 | 1.8 | |
|   | 1989 | 12 | 2042 | 369 | 1.8 | |
|   |   | 103 | 2039 | 361 | 1.8 | 3 |
|   |   | 104 | 2029 | 368 | 1.8 | 3 |
|   |   | 13 | 2021 | 356 | 1.8 | |
| 4 | 07 | 14 | 2092 | 308 | 1.5 | |
|   | June 15 | | 2062 | 296 | 1.5 | |
|   | 1989 | 16 | 2001 | 304 | 1.5 | |
|   |   | 105 | 2075 | 340 | 1.7 | 2 |
|   |   | 106 | 2004 | 350 | 1.75 | 2 |

[a]Hours after initiation of acidosis
[b]Calculation of size of 0.5% BW meals were done incorrectly in this block
[c]Not done

TABLE 12

| | | Viability data - 407A | | | | | |
|---|---|---|---|---|---|---|---|
| | | Carboy | | Combined cell susp. | | Rumen inoculant/Block | | |
| Block No. | No. | $OD_{650}$ | V.C.[a] $\times 10^8$ | Volume (ml) | V.C. $\times 10^{10}$ | Volume[b] (ml) | V.C. $\times 10^{10}$ | Est. dose $\times 10^8$ |
| 2 | A[c] | 1.345 | 4.45 | 70 | 2.41 | | | |
|   | 1 | 1.339 | ND[d] | —[e] | — | | | |
|   | 2 | 1.303 | ND | — | — | | | |
|   | 3 | 1.287 | ND | 372 | 3.41 | 221 | 1.64 | 1.20 |
| 3 | 4 | 1.266 | 4.20 | 120 | 4.20 | | | |
|   | 5 | 1.384 | 5.10 | 105 | 4.20 | | | |
|   | 6 | 1.265 | 2.60 | 137 | 7.44 | 178 | 3.21 | 1.90 |
| 4 | 7 | 1.065 | 3.21 | 100 | 3.78 | | | |
|   | 8 | 1.267 | 3.91 | 126 | 3.68 | | | |
|   | 9 | 1.292 | 4.44 | 145 | 3.19 | 185 | 3.48 | 2.15 |

[a]Viable count
[b]Per steer
[c]6 l carboy
[d]Not determined
[e]Carboys in this block were done collectively on same day

We claim:

1. A biologically pure bacterial culture of *Megasphaera elsdenii*, Agricultural Research Service Patent Culture Collection Accession Number NRRL-18624.

2. A composition for facilitating the adaptation of ruminants from a roughage or normal pasture rations to a high energy starch ration, consisting essentially of the bacterial culture of claim 1.

3. A method of facilitating the adaptation of ruminants from a roughage or normal pasture ration to a high energy ration comprising administering to said ruminant an effective amount of a bacterial culture according to claim 1 during said adaptation.

4. A method of preventing our treating acute lactic acidosis in ruminant animals comprising administering to said ruminant an amount of a bacterial culture according to claim 1 effective to prevent such acidosis.

* * * * *